United States Patent
Asahi et al.

(10) Patent No.: US 11,592,397 B2
(45) Date of Patent: Feb. 28, 2023

(54) REMOTE SUBSTANCE IDENTIFICATION DEVICE AND REMOTE SUBSTANCE IDENTIFICATION METHOD

(71) Applicant: SHIKOKU RESEARCH INSTITUTE INC., Takamatsu (JP)

(72) Inventors: Ippei Asahi, Takamatsu (JP); Sachiyo Sugimoto, Takamatsu (JP)

(73) Assignee: SHIKOKU RESEARCH INSTITUTE INCORPORATED, Kagawa (JP)

( * ) Notice: Subject to any disclaimer, the term of this patent is extended or adjusted under 35 U.S.C. 154(b) by 415 days.

(21) Appl. No.: 16/650,940

(22) PCT Filed: Sep. 27, 2018

(86) PCT No.: PCT/JP2018/035906
§ 371 (c)(1),
(2) Date: Mar. 26, 2020

(87) PCT Pub. No.: WO2019/065828
PCT Pub. Date: Apr. 4, 2019

(65) Prior Publication Data
US 2020/0271588 A1   Aug. 27, 2020

(30) Foreign Application Priority Data
Sep. 29, 2017   (JP) .............................. JP2017-189580

(51) Int. Cl.
*G02F 1/37*   (2006.01)
*G01N 21/65*   (2006.01)
(Continued)

(52) U.S. Cl.
CPC .......... *G01N 21/65* (2013.01); *G01N 33/0004* (2013.01); *G02F 1/3501* (2013.01);
(Continued)

(58) Field of Classification Search
CPC ...... G02F 1/3501; G02F 1/3503; G02F 1/353; G02F 1/37; G02F 1/39; G01N 21/65
See application file for complete search history.

(56) References Cited

U.S. PATENT DOCUMENTS

| 7,385,681 B2 | 6/2008 | Ninomiya et al. |
| 7,505,126 B2 | 3/2009 | Ninomiya et al. |

(Continued)

FOREIGN PATENT DOCUMENTS

| CN | 103076310 A | 5/2013 |
| CN | 104280671 A | 1/2015 |

(Continued)

OTHER PUBLICATIONS

Hoogen, Ricarda, "Supplemental European Search Report and Opinion", EP Application No. 18 86 3084, dated Apr. 30, 2021, 16 pages (Year: 2021).*

(Continued)

*Primary Examiner* — Daniel Petkovsek
(74) *Attorney, Agent, or Firm* — WHDA, LLP

(57) ABSTRACT

Object: To provide a remote substance identification device that can identify an unidentified substance, such as a harmful substance, from a remote location. Solution: Provided are a remote substance identification device and method, the device comprising a laser device 10 that emits a laser beam to an irradiated space; a wavelength conversion device 20 that converts a wavelength of the laser beam emitted from the laser device into a plurality of different wavelengths and that emits laser beams of the different wavelengths to the irradiated space; a light collecting-detecting device 30, 40, 50 that collects and detects resonance Raman-scattered light generated from an irradiated object due to resonance Raman (Continued)

scattering; and a processor 60 that identifies the irradiated object on the basis of a result detected by the collecting-detecting device 30, 40, 50.

15 Claims, 7 Drawing Sheets

(51) Int. Cl.
　　*G01N 33/00*　　(2006.01)
　　*G02F 1/35*　　(2006.01)
　　*G02F 1/39*　　(2006.01)
　　*G02F 1/355*　　(2006.01)
(52) U.S. Cl.
　　CPC ............ *G02F 1/353* (2013.01); *G02F 1/3503* (2021.01); *G02F 1/37* (2013.01); *G02F 1/39* (2013.01); *G01N 2021/653* (2013.01); *G01N 2201/06113* (2013.01); *G02F 1/354* (2021.01); *G02F 1/3507* (2021.01); *G02F 1/3551* (2013.01)

(56) References Cited

U.S. PATENT DOCUMENTS

| | | | |
|---|---|---|---|
| 7,656,526 B1* | 2/2010 | Spuler | G01N 21/538 356/336 |
| 9,116,243 B1 | 8/2015 | Brown | |
| 2017/0299512 A1* | 10/2017 | Hunter | G01N 21/65 |
| 2019/0120753 A1* | 4/2019 | Prater | H01J 37/26 |

FOREIGN PATENT DOCUMENTS

| | | | | |
|---|---|---|---|---|
| CN | 104849257 A | | 8/2015 | |
| JP | 3783019 B2 | | 6/2006 | |
| WO | WO-2017116998 A1 | * | 7/2017 | ............ G01J 3/0208 |

OTHER PUBLICATIONS

Willitsford, Adam et al, "Resonance Raman measurements utilizing a deep UV source", Proceedings of Spie, 2008, vol. 6950, pp. 69500A-1 to 69500A-8; Cited in ISR. (8 pages).
International Search Report dated Dec. 25, 2018, issued in counterpart application No. PCT/JP2018/035906. (2 pages).
International Preliminary Report on Patentability (Form PCT/IPEA/409) issued in counterpart International Application No. PCT/JP2018/035906. (5 pages).
Ehlerding, A. et al, Resonance-Enhanced Raman Spectroscopy on Explosives Vapor at Standoff Distances, International Journal of Spectroscopy, 2012, pp. 1 to 9, vol. 2012, ID 158715, cited in Supplementary European Search Report dated Apr. 30, 2021. (10 pages).
Johansson, I. et al, Stand-off detection of explosives vapors by resonance-enhanced Raman spectroscopy, Roceedings of SPIE, 2013, pp. 87090N-1 to 87090N-10, vol. 8709, cited in Supplementary European Search Report dated Apr. 30, 2021. (11 pages).
Hallen, H. D. et al: Atmospheric Absorption versus Deep Ultraviolet (Pre-) Resonance in Raman LIDAR Measurements, Proceedings of SPIE, 2016, pp. 983210-1 to 983210-11, vol. 9832, SPIE, US, cited in Supplementary European Search Report dated Apr. 30, 2021. (11 pages).
Chadwick, C. T. et al, Deep ultraviolet Raman spectroscopy: A resonance-absorption trade-off illustrated by diluted liquid benzene, Journal of Applied Physics, Dec. 22, 2015, pp. 243101-1 to 243101-6, vol. 118, 243101, American Institute of Physics, US, cited in Supplementary European Search Report dated Apr. 30, 2021. (6 pages).
Liner, D. A. V. et al, Efficient second, third, fourth, and fifth harmonic generation of a Yb-doped fiber amplifier, Optics Communications, Sep. 15, 2002, pp. 393 to 398, vol. 210, Elsevier, Amsterdam, NL, cited in Supplementary European Search Report dated Apr. 30, 2021. (6 pages).
Butt, N. R. et al, Classification of Raman Spectra to Detect Hidden Explosives, IEEE Geoscience and Remote Sensing Letters, May 2011, pp. 517 to 521, vol. 8, No. 3, IEEE Service Center, New York, NY, US, cited in Supplementary European Search Report dated Apr. 30, 2021. (5 pages).
Rosen, H. et al, Remote detection of pollutants using resonance Raman scattering, Applied Optics, Nov. 1975, pp. 2703 to 2706, vol. 14, No. 11, cited in Supplementary European Search Report dated Apr. 30, 2021. (4 pages).
Supplementary European Search Report dated Apr. 30, 2021, issued in counterpart EP Application No. EP18863084. (3 pages).
Sakuma, Jun, "Method for using laser by wavelength conversion" OPTRONICS, 2003, No. 9, pp. 155-160; Cited in ISR. (10 pages).
Office Action dated Sep. 9, 2022, issued in counterpart CN application No. 201880061675.3, with English translation. (11 pages).

* cited by examiner

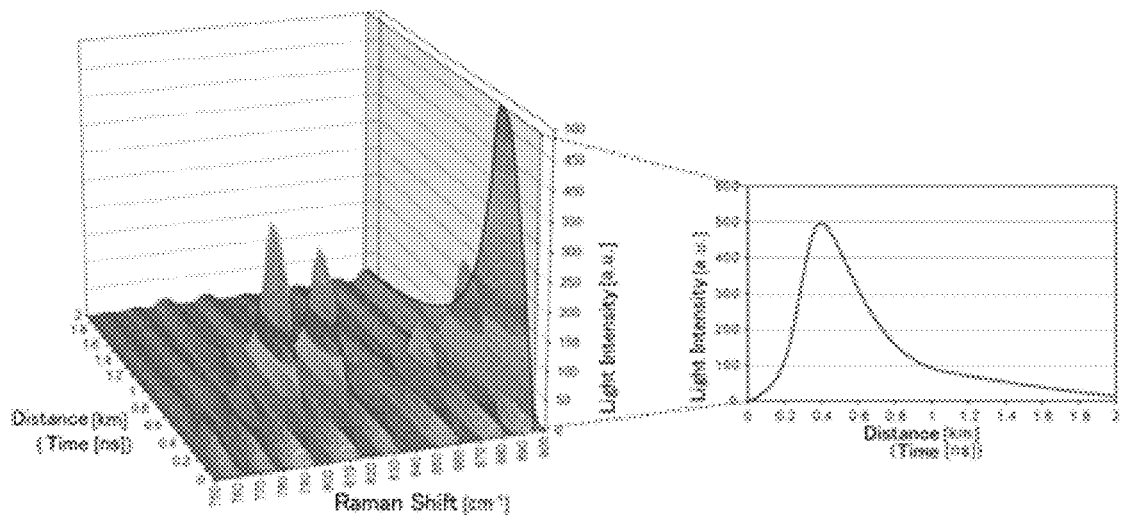
Fig. 9(A)    Fig. 9(B)
Fig. 10
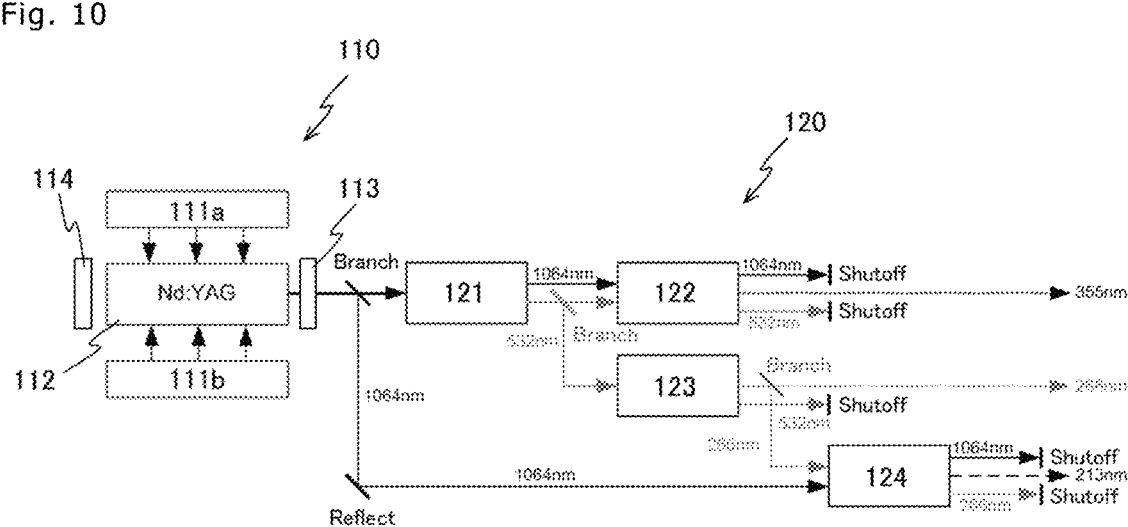

REMOTE SUBSTANCE IDENTIFICATION DEVICE AND REMOTE SUBSTANCE IDENTIFICATION METHOD

TECHNICAL FIELD

The present invention relates to a remote substance identification device and a remote substance identification method each of which remotely identifies an unidentified substance, such as a harmful substance, by utilizing resonance Raman scattering.

BACKGROUND ART

A technique of identifying a harmful substance, such as flammable gas, from a remote location has been demanded up to now. The Raman scattering spectroscopy (laser Raman method) is known as a method of identifying that type of substance. Raman scattering is a phenomenon that, when a molecule is irradiated with monochromatic light, a frequency of scattered light is shifted by a vibration frequency specific to the molecule. An amount of the frequency shift of the scattered light is a variable specific to the substance. Accordingly, when a substance as a measurement target is irradiated with a laser beam of a predetermined wavelength, Raman-scattered light having wavelength different from the wavelength of the laser beam is generated from the substance irradiated with the laser beam. Whether the target substance is present or not can be identified by analyzing the Raman-scattered light. Furthermore, because the intensity of the Raman-scattered light is proportional to a density of the target substance, a concentration of the target substance can be measured from the detected intensity of the Raman-scattered light. In addition, it is known that, when the laser wavelength matches with a resonance excitation wavelength specific to the substance, Raman-scattered light (hereinafter called "resonance Raman-scattered light" in some cases) with intensity much higher than that of normal Raman-scattered light (non-resonance Raman-scattered light) is generated by a resonance effect.

There is known a method of monitoring a specific substance from a remote location by utilizing the above-described Raman-scattered light. For example, Patent Document 1 discloses a gas leakage monitoring method of emitting a laser beam to a monitoring target space, collecting Raman-scattered light corresponding to the wavelength of measurement target gas, and determining, in the form of an image, a spatial intensity distribution of the collected Raman-scattered light, thus visualizing the presence of the leaked gas.

CITATION LIST

Patent Documents

Patent Document 1: Japanese Patent No. 3783019

SUMMARY OF INVENTION

Technical Problem

The related art can detect whether the substance, i.e., the measurement target, is present or not, or can measure the concentration of the substance, i.e., the measurement target, by collecting the Raman-scattered light corresponding to the substance, i.e., the measurement target. However, the related art cannot identify an unidentified substance from a remote location.

An object of the present invention is to provide a remote substance identification device that can identify an unidentified substance, such as a harmful substance, from a remote location.

Solution to Problem

The present invention provides a remote substance identification device comprising a laser device including an oscillator that emits a laser beam of a particular wavelength, a light collecting-detecting device that collects and detects resonance Raman-scattered light from an irradiated space, and a processor that identifies an irradiated object present in the irradiated space on the basis of a result detected by the light collecting-detecting device, wherein the remote substance identification device further comprises a wavelength conversion device that converts a wavelength of the laser beam emitted from the laser device into a plurality of different wavelengths and that emits laser beams of the different wavelengths to the irradiated space.

The oscillator may be an oscillator oscillating the laser beam in a wavelength range higher than an ultraviolet range, and the wavelength conversion device may convert a wavelength of the laser beam oscillated from the oscillator into an excitation wavelength in the ultraviolet range.

The remote substance identification device may further comprise a scanning device that scans the irradiated space with the laser beams emitted from the wavelength conversion device, and the processor may further measure a location of the irradiated object on the basis of the result detected by the light collecting-detecting device.

The wavelength conversion device may include a wavelength converter to which the laser beam oscillated from the oscillator is input, and a rotating device that changes an inclination angle of the wavelength converter relative to an optical axis continuously or discontinuously in a stepwise manner.

The wavelength conversion device may include a second-higher harmonic generator that converts the laser beam oscillated from the oscillator into a second-higher harmonic laser beam and outputs the converted second-higher harmonic laser beam, a third-higher harmonic generator that converts the laser beam output from the second-higher harmonic generator into a third-higher harmonic laser beam and outputs the converted third-higher harmonic laser beam, and a fourth-higher harmonic generator that converts the laser beam output from the third-higher harmonic generator into a fourth-higher harmonic laser beam and outputs the converted fourth-higher harmonic laser beam.

The wavelength conversion device may include a fifth-higher harmonic generator that converts the laser beam output from the fourth-higher harmonic generator into a fifth-higher harmonic laser beam and outputs the converted fifth-higher harmonic laser beam.

The remote substance identification device may comprise a plurality of irradiation systems each including the laser device and the wavelength conversion device, the irradiation systems emitting laser beams of which wavelengths do not overlap with each other.

The processor may include a storage device that previously stores an excitation profile representing a feature pattern of the resonance Raman-scattered light at an excitation wavelength for each substance, and the processor may identify the irradiated object by comparing the result detected by the light collecting-detecting device and the excitation profile.

The light collecting-detecting device may include a first optical filter allowing only a first wavelength range to pass therethrough and a second optical filter allowing only a second wavelength range to pass therethrough, the second wavelength range having a center wavelength different from that of the first wavelength range, and the processor may identify the irradiated object on the basis of a correspondence relationship between the wavelength range passing through each of the optical filters and a wavelength of the resonance Raman-scattered light generated from each irradiated object.

The processor may measure a concentration of the irradiated object on the basis of the intensity of the detected Raman-scattered light from the irradiated object.

The irradiated object may be a gaseous harmful substance, a liquid harmful substance, a solid harmful substance, or a harmful microorganism.

The present invention further provides a remote substance identification method of emitting a laser beam to an irradiated space, collecting and detecting resonance Raman-scattered light from an irradiated object present in the irradiated space, and determining a location of the irradiated object on the basis of the resonance Raman-scattered light, the remote substance identification method comprising steps of emitting laser beams of different wavelengths, and identifying the irradiated object on the basis of detected results of the resonance Raman-scattered light generated upon irradiation with the laser beams of the different wavelengths.

The irradiated space may be an outdoor space, and the location and a concentration of the irradiated object present in the irradiated space may be detected by scanning the irradiated space with the laser beams.

Advantageous Effect of Invention

According to the present invention, an unidentified substance, such as a harmful substance, can be identified from a remote location.

BRIEF DESCRIPTION OF THE DRAWINGS

FIG. 9 is a graph depicting a time-dependent waveform of a resonance Raman spectrum.

FIG. 10 is a block diagram of a laser device and a wavelength conversion device according to a first modification.

DESCRIPTION OF EMBODIMENTS

A remote substance identification device according to the present invention detects a harmful substance from a remote location and performs identification of the substance and measurement of a concentration of the substance (hereinafter simply called "identification" in some cases). Examples of the harmful substance identifiable by the remote substance identification device according to the present invention include (1) air pollutants such as SOx and NOx, (2) flammable substances such as hydrogen, methane, propane, and gasoline, (3) odorous components such as ammonia and hydrogen carbide, (4) pesticide-agrochemical components such as acephate and malathion, (5) nerve agents such as VX, tabun, and sarin, (6) blood agents such as cyanogen chloride and hydrogen cyanide, and asphyxiants such as phosgene, (7) blister agents such as sulfur mustard gas and lewisite, (8) explosives such as TNT and HNIW, and (9) harmful microorganisms such as anthrax, Ebola virus, and smallpox virus. Furthermore, the remote substance identification device according to the present invention can be utilized to identify a variety of harmful substances regardless of states (gas, liquid, and solid) of the harmful substances and regardless of whether harmful substances are living or inanimate matters.

Figure 1:
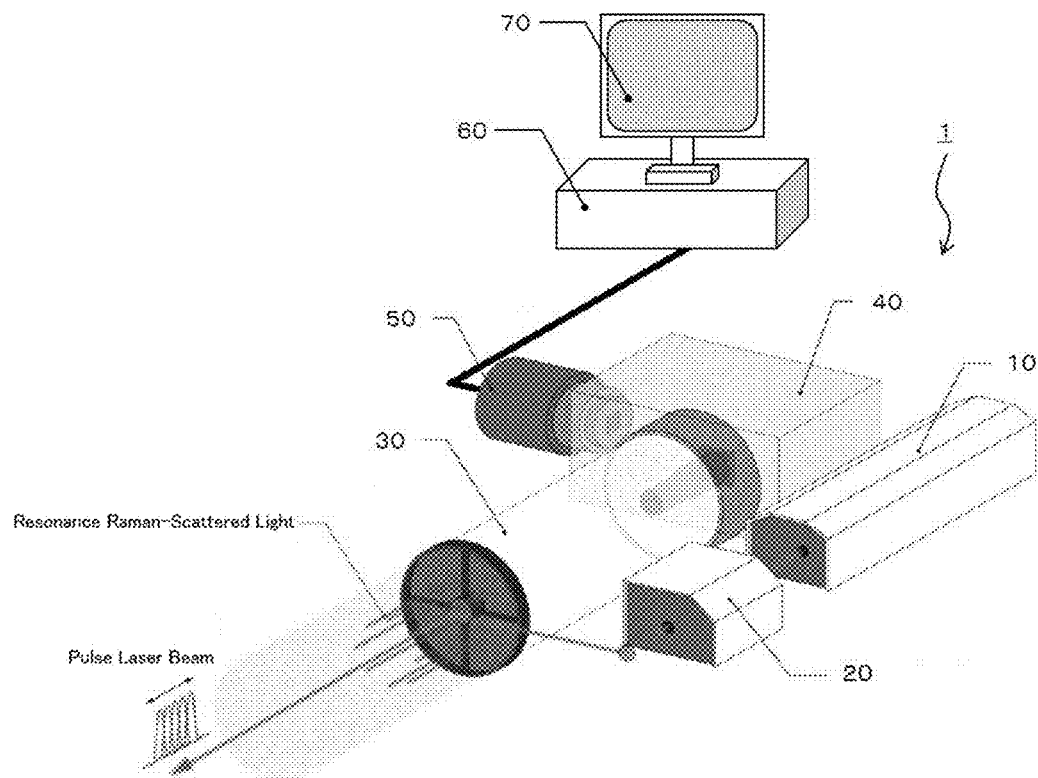
FIG. 1 is a perspective view of a remote substance identification device according to an embodiment.

FIG. 1 is a perspective view of a remote substance identification device 1 according to an embodiment. As illustrated in FIG. 1, the remote substance identification device 1 according to this embodiment includes a laser device 10, a wavelength conversion device 20, a light collecting optical system 30, a spectrometric instrument 40, an optical detector 50, a processor 60, and a display device 70. In the remote substance identification device 1, as illustrated in FIG. 1, a pulse laser beam oscillated from the laser device 10 is emitted to an irradiated object after a wavelength of the beam is converted into predetermined ultraviolet wavelengths by the wavelength conversion device 20. Raman-scattered light generated from the irradiated object is collected by the light collecting optical system 30, is detected by the spectrometric instrument 40 and the optical detector 50, and is analyzed by the processor 60. A result of the analysis is displayed on the display device 70. In this embodiment, the remote substance identification device 1 has the LIDAR (Light Detection and Ranging) function of sensing a surrounding space. The above-mentioned components will be described below one by one.

The laser device 10 oscillates and emits the laser beam for irradiation to the irradiated object. A Nd:YAG laser, which is a pulse laser source, is used as the laser device 10 in this embodiment, but the laser device is not limited to such an example. The Nd:YAG laser outputs a pulse laser beam of 1064 nm as a fundamental wave with a pulse width of several to several tens of ns and a repetition frequency of 10 Hz to several kHz. The laser beam emitted from the laser device 10 is input to the wavelength conversion device 20.

Figure 2:
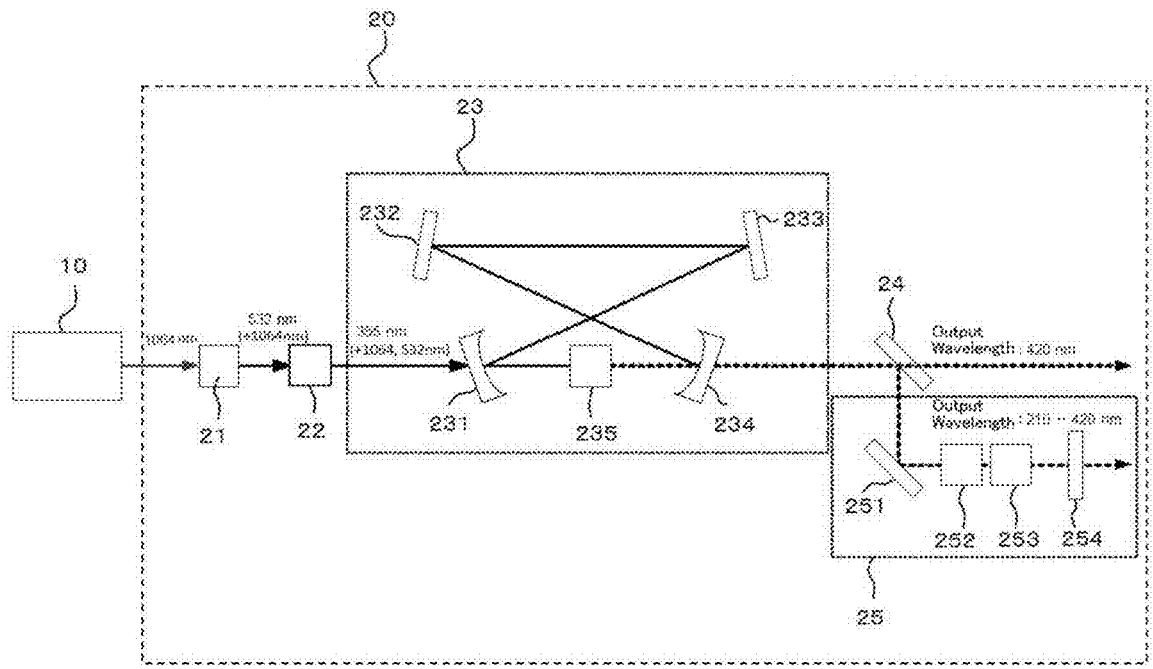
FIG. 2 is a block diagram illustrating details of a laser device and a wavelength conversion device both constituting the remote substance identification device according to the embodiment.

The wavelength conversion device 20 converts a wavelength of the laser beam to be emitted to the irradiated object (space). In this embodiment, the wavelength conversion device 20 converts the wavelength of the laser beam that is the fundamental wave, and successively emits laser beams of different wavelengths to the irradiated object. Therefore, the irradiated object can be identified on the basis of Raman-scattered light that is generated upon irradiation with the laser beam of the corresponding wavelength. As illustrated in FIG. 2, the wavelength conversion device 20 includes LBO crystals 21 and 22, a first optical parametric oscillator 23, a total reflection mirror 24, and a second optical parametric oscillator 25.

A laser beam having wavelength of 1064 nm emitted from the laser device 10 is first input to the LBO crystal 21 for conversion (frequency multiplication) into a laser beam of 532 nm. Then, the laser beams of 1064 nm and 532 nm after passing through the LBO crystal 21 are input to the LBO crystal 22 for conversion (frequency multiplication) into a laser beam of 355 nm. Thereafter, the laser beams of 1064 nm, 532 nm, and 355 nm after passing through the LBO crystal 22 are input to the first optical parametric oscillator 23.

The first optical parametric oscillator 23 mainly includes a dichroic concave mirror 231, total reflection mirrors 232 and 233, a concave output mirror 234, and a BBO crystal 235.

Of the laser beams input to the first optical parametric oscillator 23, only the laser beam of 355 nm passes through the dichroic concave mirror 231. The laser beam of 355 nm having passed through the dichroic concave mirror 231 is input to the BBO crystal 235 for wavelength conversion. The BBO crystal 235 is held on a rotating device (not illustrated) and is rotated under control of the processor 60 to change an inclination angle relative to an optical axis of the laser beam continuously or discontinuously in a stepwise manner. The laser beam of 355 nm can be thereby changed to laser beams of different wavelengths continuously or discontinuously in a stepwise manner.

The laser beam having passed through the BBO crystal 235 enters the concave output mirror 234. The concave output mirror 234 is not a total reflection mirror and it allows a laser beam of a particular wavelength to pass therethrough and reflects the remaining laser beam. The laser beam having been reflected by the concave output mirror 234 is reflected by the total reflection mirrors 232 and 233 and further reflected by the dichroic concave mirror 231, and then enters the concave output mirror 234 again after passing through the BBO crystal 235. As a result, the laser beam input to the first optical parametric oscillator 23 is amplified and output from the first optical parametric oscillator 23.

In this embodiment, the first optical parametric oscillator 23 converts the laser beam of 355 nm into the laser beam having wavelength of 420 nm or longer and emits the latter. Therefore, when the target wavelength of the laser beam is 420 nm or longer, the laser beam is output from the first optical parametric oscillator 23 and then directly output from the wavelength conversion device 20, as illustrated in FIG. 2. On the other hand, when the target wavelength of the laser beam is shorter than 420 nm, the laser beam output from the first optical parametric oscillator 23 is totally reflected by the total reflection mirror 24 and then input to the second optical parametric oscillator 25.

As illustrated in FIG. 2, the second optical parametric oscillator 25 includes a total reflection mirror 251, BBO crystals 252 and 253, and an output mirror 254. In the second optical parametric oscillator 25, the wavelength of the laser beam having been converted by the first optical parametric oscillator 23 is converted into a double frequency. For example, when the wavelength of the laser beam having been converted by the first optical parametric oscillator 23 is 420 nm, a wavelength of a laser beam output from the second optical parametric oscillator 25 is 210 nm. When the wavelength of the laser beam output from the second optical parametric oscillator 25 is to be 300 nm, it is just required that the wavelength of the laser beam output from the first optical parametric oscillator 23 is set to 600 nm. The laser beam output from the second optical parametric oscillator 25 is output from the wavelength conversion device 20 and is emitted to the irradiated objected (space) as illustrated in FIG. 1.

Here, when the wavelength of the laser beam output from the wavelength conversion device 20 is a wavelength at which resonance Raman scattering is generated from the irradiated object, resonance Raman-scattered light with much higher intensity than non-resonance Raman scattering is generated. The non-resonance Raman scattering is generated from almost all molecules except for monoatomic molecules, but the intensity of the scattered light is very weak. On the other hand, an increase rate of scattering cross section (value indicating probability of scattering, i.e., index of scattering intensity per molecule) obtained with the resonance Raman scattering is theoretically $10^4$ to $10^6$ times that obtained with the non-resonance Raman scattering, the intensity of the resonance Raman-scattered light is significantly higher than that of the non-resonance Raman-scattered light. In this embodiment, the irradiated object can be detected with high accuracy by detecting the resonance Raman-scattered light.

The resonance Raman-scattered light generated at a remote location upon irradiation with the laser beam is, as illustrated in FIG. 1, collected by the light collecting optical system (telescope) 30 with high efficiency and is input to the spectrometric instrument 40.

The spectrometric instrument 40 includes, e.g., a diffraction grating spectrometer or prism spectrometer and disperses incident light in a particular range, the dispersed light being input to the optical detector 50.

The optical detector 50 includes a photosensor for detecting the light intensity per wavelength. The photosensor may be constituted by one photosensor (e.g., an avalanche photodiode or a photomultiplier), or may be a multichannel sensor (e.g., a CCD sensor or a CMOS sensor) that is constituted by a plurality of photosensor.

The processor 60 includes a storage device storing resonance Raman data for each of harmful substances described later and an analysis program, and a CPU (Central Processing Unit) operating as an operation circuit that executes the analysis program. The processor 60 identifies the harmful substance by comparing an excitation profile of the harmful substance (mixture), i.e., the irradiated object, which has been obtained by the spectrometric instrument 40 and the optical detector 50, and the excitation profile for each of the harmful substances, which is previously stored in the storage device. Details of a method of identifying the harmful substance will be described later. The processor 60 further controls the laser oscillation by the laser device 10, the wavelength of the laser beam converted by the wavelength conversion device 20, etc. FIG. 1 illustrates an example in which the processor 60 is constituted by a personal computer connected by a wire cable, but the configuration of the processor 60 is not limited to the illustrated example. In another example, the processor 60 may be constituted by a computer that is installed at a remote location and is connected for communication via a network (including the Internet and a wireless communication network), for example. Alternatively, the functions of the processor 60 may be distributed and installed into a plurality of computers.

The display device 70 includes a monitor (display screen) displaying specific information of the harmful substance (such as the name of the identified harmful substance, the resonance Raman spectrum, and the concentration), the specific information having been obtained by the processor 60. A display method used in the display device 70 is not limited to particular one. By superimposing the location and the concentration of the harmful substance, as image information, on an image captured by a camera (e.g., by coloring a portion of the captured image corresponding to the location of the harmful substance with a color depending on the type of the harmful substance and its concentration), the information of the harmful substance can be displayed such that a user can intuitively recognize the information of the harmful substance. A method of superimposing the information of the harmful substance on the captured image is not limited to particular one, and known methods can be optionally used.

A method identifying the harmful substance, i.e., a target to be detected, will be described below. The following Table 1 lists wavelengths at which the resonance Raman-scattered lights are generated from various harmful substances. As seen from Table 1, in the case of, for example, chloroform that is an anesthetic, the resonance Raman-scattered light is generated upon irradiation with the laser beam having wavelength of 210 to 220 nm.

denotes cyclosarin, and DIMP denotes a mimic. As seen from FIG. 3(B), any of the nerve agents depicted in the graph has light absorption in a deep ultraviolet wavelength range not longer than 250 nm. Therefore, the resonance enhancement occurs in Raman scattering by exciting the nerve agents with the laser beam in the deep ultraviolet wavelength range not longer than 250 nm.

Figure 3A:
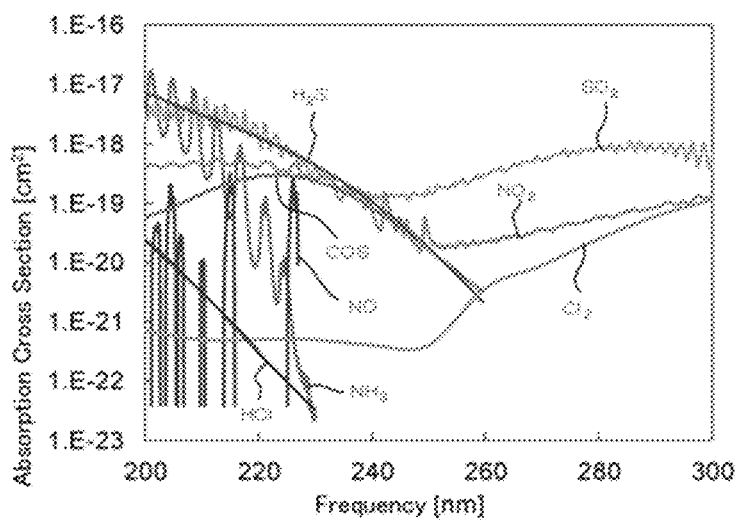
FIG. 3 is a graph depicting ultraviolet absorption characteristics of air pollutants and nerve agents.
Figure 3B:
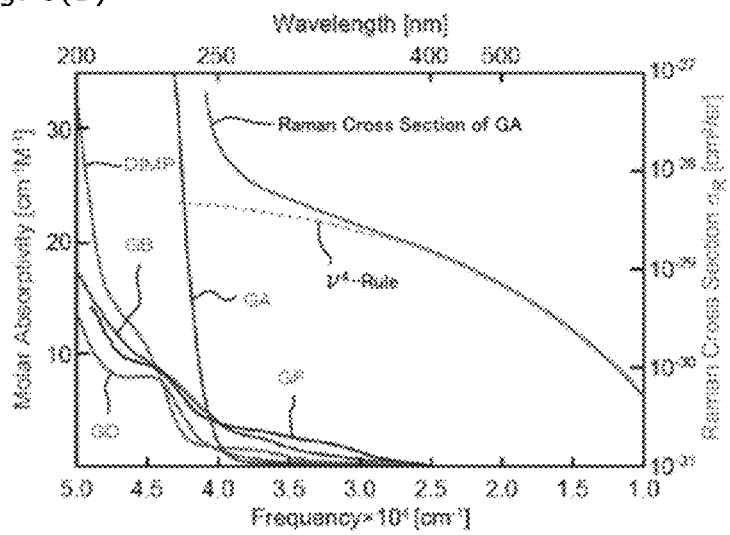

Thus, since many harmful substances exhibit light absorptions in the ultraviolet-visible light range, i.e., electron energy level transitions, the resonance enhancement of Raman scattering with the Raman effect occurs in the ultraviolet-visible light range. FIG. 3(B) depicts a relationship between a Raman cross section and a wavelength of GA (tabun), for example. Usually, according to the $v^4$-rule that is a general rule, the intensity of the scattered light increases in proportion to one of the fourth power of the excitation wavelength. In the case of GA (tabun), however, because the resonance enhancement occurs in the Raman scattering in the deep ultraviolet wavelength range shorter than about 250 nm, the Raman-scattered light (resonance Raman-scattered light) is significantly enhanced as depicted in FIG. 3(B). Accordingly, in this embodiment, high-sensitivity measurement with the enhancement of the Raman scattering can be performed for a variety of harmful substances by detecting the resonance Raman-scattered light.

The inventors selected two samples, i.e., acephate as an insecticide component that is used as a mimic of the nerve agent, and a phosphoric acid in consideration of only the P—O bond that is a core of the insecticide component from

TABLE 1

| Classification | Substance Name | Sweep Wavelength (nm) | | | | |
| --- | --- | --- | --- | --- | --- | --- |
| Anesthetic | chloroform | 210-222 | | | | |
| Toxic Gas | hydrogen sulfide | 210-253 | | | | |
| | sulfur disulfide | 210.5-211 | 212-213 | 213.5-214.5 | 215.5-216 | 270-310 |
| | nitrogen monoxide | 214-216 | 225-227 | | | |
| | ammonia | 212-213 | 216-217 | 220.5-221.5 | | |
| | chlorine | 271-400 | | | | |
| | carbonyl sulfide | 210-253 | | | | |
| Explosive | trinitrotoluene | 210-300 | | | | |
| Blood Agent | arsine | 210-230 | | | | |
| Incendiary | chlorine trifluoride | 210-328 | | | | |
| Asphyxiant | phosgene | 210-273 | | | | |
| | chloropicrin | 210-322 | | | | |
| Nerve Agent | tabun | 210-240 | | | | |
| | sarin | 210-280 | | | | |
| | soman | 210-250 | | | | |
| | cyclosarin | 210-300 | | | | |

Whether resonance enhancement with the Raman effect occurs for the irradiated object can be estimated by observing ultraviolet-visible light absorption characteristics of the irradiated object. FIG. 3(A) is a graph depicting ultraviolet absorption characteristics of typical air pollutants, etc. Light absorption in an ultraviolet-visible light range represents a distribution of electron transition energy specific to a substance. Taking ammonia ($NH_3$) as an example, the ammonia exhibits a distribution of electron transition energy, the distribution having a plurality of peaks in a range of 200 to 230 nm. By exciting the ammonia ($NH_3$) with the laser beam in the range of 200 to 230 nm, therefore, the resonance enhancement occurs in Raman scattering caused by the ammonia ($NH_3$).

Figure 4:
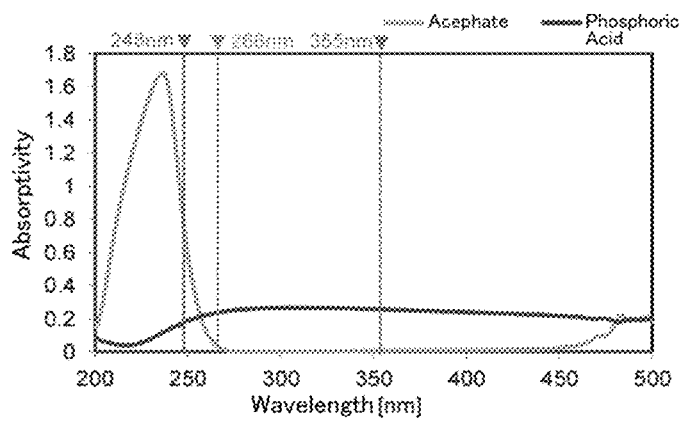
FIG. 4 is a graph depicting ultraviolet-visible light absorption characteristics of acephate and a phosphoric acid.

Furthermore, FIG. 3(B) is a graph depicting ultraviolet absorption characteristics of nerve agents. In the graph, GA denotes tabun, GB denotes sarin, GD denotes soman, GF the viewpoint of chemical structure, and observed the resonance Raman scattering of those samples. FIG. 4 represents a result of the observation, namely a graph depicting ultraviolet-visible light absorption characteristics of the acephate and the phosphoric acid.

As seen from FIG. 4, the acephate and the phosphoric acid have absorption spectra in an ultraviolet range. This implies that the acephate and the phosphoric acid exhibit the electron energy level transitions in the ultraviolet range. In more detail, the absorption spectrum of the acephate is featured in sharply rising toward the shorter wavelength side from the vicinity of 250 nm and quickly attenuating after reaching a peak near 240 nm. On the other hand, absorptivity of the phosphoric acid gradually increases from the vicinity of 250 nm on the longer wavelength side and exhibits a relatively broad distribution until near 500 nm. From the above-described features, it is thought that significant enhancement of the resonance Raman effect, i.e., a significant increase of the Raman cross section, is caused by exciting the acephate and the phosphoric acid with the laser beam of the wavelength at which the absorptivity is relatively high.

Figure 5A:
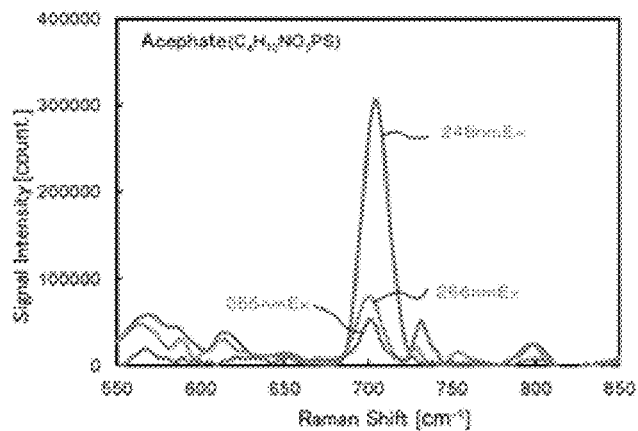
FIG. 5 is a graph depicting resonance spectra of the acephate and the phosphoric acid.
Figure 5B:
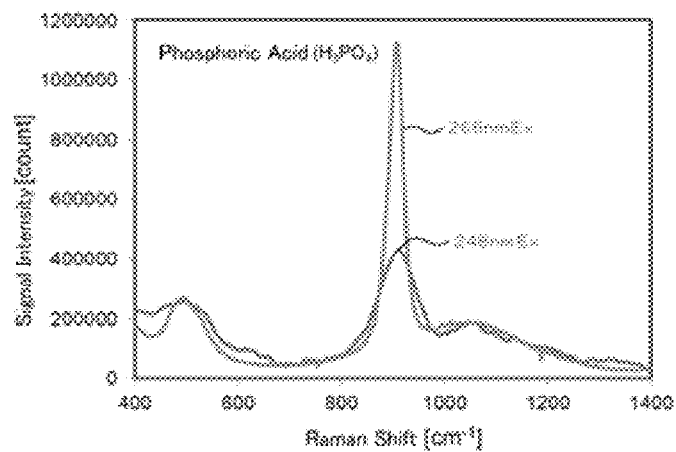

From the above-described point of view, the inventors conducted experiments of exciting the acephate and the phosphoric acid by using three wavelengths in the ultraviolet range, i.e., a third-harmonic (355 nm) and a fourth-harmonic (266 nm) of an Nd:YAG laser and 248 nm of an excimer laser, and compared results of the experiments. FIG. 5(A) is a graph depicting a resonance Raman spectrum of the acephate, and FIG. 5(B) is a graph depicting a resonance Raman spectrum of the phosphoric acid. It is to be noted that those resonance spectra depict only spectral components resulting from the resonance enhancement in order to exclude an influence of the enhancement according to the $v^4$-rule of the Raman cross section.

As seen from FIG. 5(A), in the case of the acephate, a peak near a Raman shift of 700 $cm^{-1}$ is significantly enhanced by the excitation with the laser beam of 248 nm. Furthermore, as seen from an example depicted in FIG. 5(B), in the case of the phosphoric acid, a peak near a Raman shift of 900 $cm^{-1}$ is significantly enhanced by the excitation with the laser beam of 266 nm. Thus, it has been proved, as previously estimated by the inventors, that the Raman-scattered light is significantly enhanced by the excitation with the laser beam having the wavelength (e.g., 248 nm for the acephate and 266 nm for the phosphoric acid) at which light absorptions in the ultraviolet-visible light range, i.e., electron energy level transition, occurs. Although an enhancement factor in each of the depicted resonance Raman spectra does not reach a theoretical value ($10^4$ times or more), this is presumably attributable to the fact that, at the wavelengths used in the experiments, the acephate and the phosphoric acid are in a pre-stage resonance state and they are not in an intrinsic resonance state. Hence it deems that further enhanced peaks are obtained by exciting the acephate and the phosphoric acid with the laser beams having the wavelengths at which they cause the intrinsic resonance.

As described above, by previously specifying, from the ultraviolet-visible light absorption characteristics of the harmful substance, the wavelength of the laser beam at which the Raman-scattered light from the harmful substance is enhanced, and by storing data representing what resonance Raman spectrum is obtained at which wavelength, the harmful substance can be identified from data of the resonance Raman spectrum obtained when the laser beam of the specified wavelength is emitted.

Figure 6:
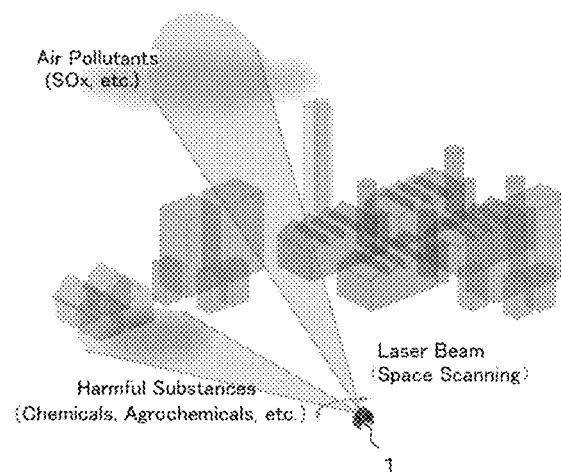
FIG. 6 is an illustration referenced to explain a remote substance identification method using the remote substance identification device according to the embodiment.

FIG. 6 is an illustration referenced to explain a method of utilizing the remote substance identification device 1. Although a place where the remote substance identification device 1 is used may be outdoors or indoors, FIG. 6 illustrates the case in which the remote substance identification device is used outdoors to detect and identify harmful substances including air pollutants, chemicals, agrochemicals, etc. The remote substance identification device 1 is mounted on a scanning device (not illustrated), and an emission direction of the laser beam is varied by the scanning device under control of the processor 60 to be able to scan an irradiated space (vertically and horizontally, or in a panning and tilting manner). The remote substance identification device 1 repeatedly performs operation of emitting laser beams of different wavelengths the prescribed number of times in a first direction (X1, Y1) in the irradiated space, then emitting the laser beams of the different wavelengths the prescribed number of times in a second direction (X1, Y2 or X2, Y1) in continuity with the first direction (X1, Y1), and further similarly emitting the laser beams of the different wavelengths the prescribed number of times for each of third and subsequent directions different from the first and second directions. As a result, the remote substance identification device 1 can identify the locations and the concentrations of the harmful substances in the irradiated space. Alternatively, the remote substance identification device 1 may repeatedly perform operation of scanning the irradiated space with a laser beam of a first wavelength, then scanning the irradiated space with a laser beam of a second wavelength different from the first wavelength, and further similarly scanning the irradiated space with each of laser beams of third and subsequent wavelengths different from the first and second wavelengths.

For example, the remote substance identification device 1 continuously converts the laser beam emitted from the laser device 10 into laser beams having different wavelengths in the ultraviolet range by the wavelength conversion device 20, and emits the laser beams to the irradiated space at a certain azimuth. Moreover, the remote substance identification device 1 collects resonance Raman-scattered lights, which have been generated upon excitation with the emitted laser beam, by the light collecting optical system 30, detects the resonance Raman-scattered light by the spectrometric instrument 40 and the optical detector 50, and obtains a resonance Raman spectrum by the processor 60 on the basis of the detected resonance Raman-scattered light. When what kinds of harmful substances are present in the irradiated space are estimated to some extent, the laser beam may be emitted for identification of the harmful substances by discontinuously converting the wavelength of the laser beam into different wavelengths in a stepwise manner, because it is more effective to emit the wavelength in a particular range. As an alternative, a time required for the substance identification may be shortened by installing a plurality of irradiation systems each of which is constituted by the laser device 10 and the wavelength conversion device 20, and by emitting laser beams of different wavelengths from the individual irradiation systems.

When most of the substances present in the irradiated space are each made of a single component, each substance can be identified by specifying a peak wavelength of the resonance Raman-scattered light.

When the substance present in the irradiated space is made of a mixture, the mixture is identified by forming an excitation profile. When a plurality of harmful substances are mixed and interfere with each other, a resonance Raman spectrum is given by adding resonance Raman spectra of the individual harmful substances.

With the related-art method of observing the non-resonance Raman scattering, because a mixture needs to be identified by using a two-dimensional Raman spectrum, substances having analogous chemical structures exhibit very close spectrum waveforms, and it is difficult to discriminate those substances. On the other hand, even the substances having analogous chemical structures can be discriminated by using an excitation profile that is formed by three-dimensional data added with enhancement characteristics of the Raman-scattered light depending on change of the excitation wavelength.

Figure 7A:
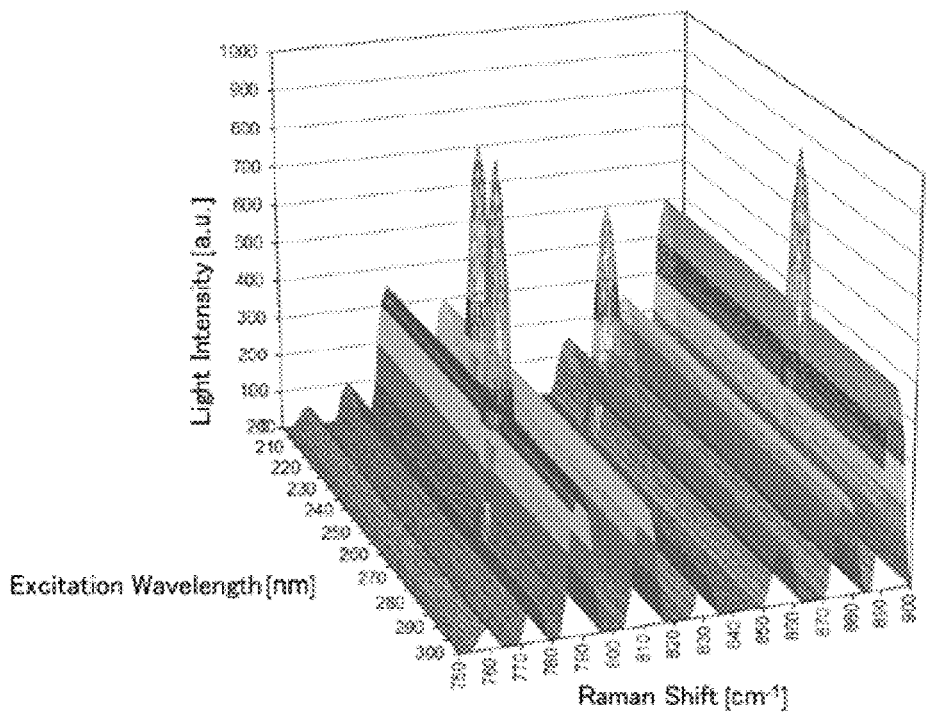
FIG. 7(A) depicts an excitation profile of a mixture A.
Figure 7B:
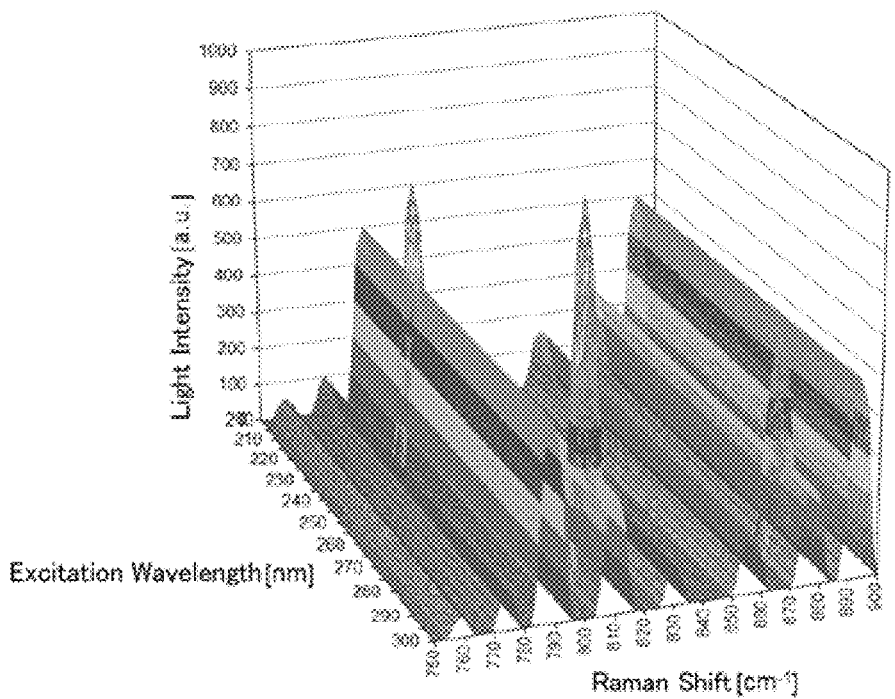
FIG. 7(B) depicts an excitation profile of a mixture B.
Figure 8A:
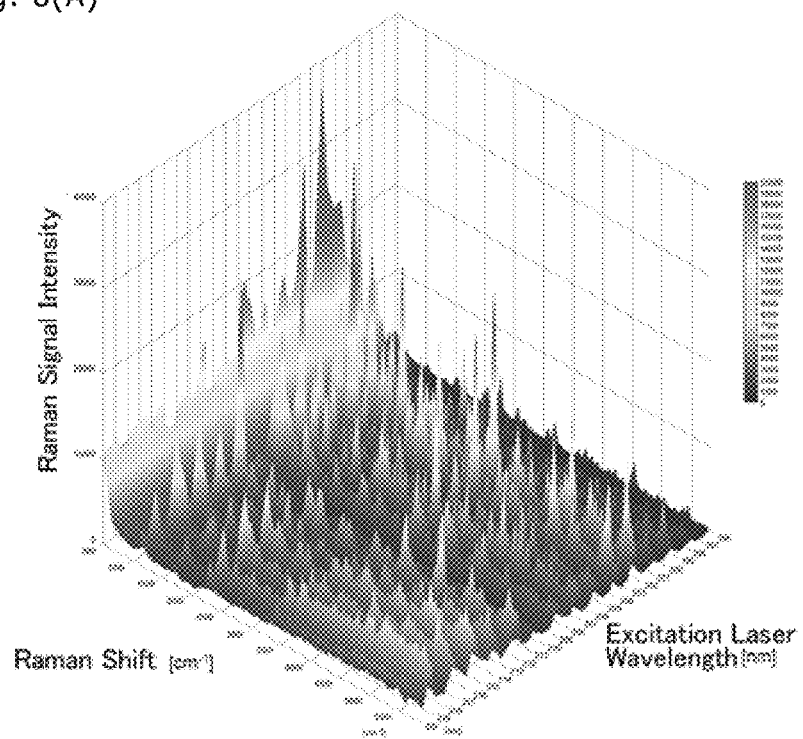
FIG. 8(A) depicts a resonance Raman excitation profile of $SO_2$.
Figure 8B:
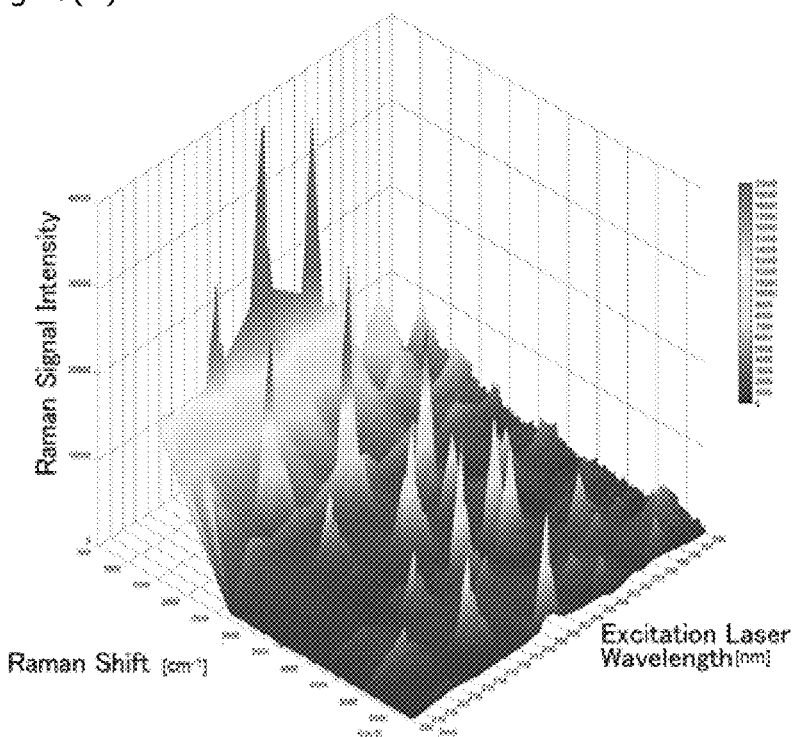
FIG. 8(B) depicts a resonance Raman excitation profile of $NH_3$.

FIG. 7(A) depicts an excitation profile of a mixture A, and FIG. 7(B) depicts an excitation profile of a mixture B having a chemical structure analogous to that of the mixture A. FIG. 8(A) depicts a resonance Raman excitation profile of $SO_2$, and FIG. 8(B) depicts a resonance Raman excitation profile of $NH_3$.

The processor 60 can identify a detected mixture by determining a matching degree with excitation profile data of mixtures previously stored in the storage device. In this embodiment, the processor 60 can separate and identify individual harmful substances by executing a multivariable analysis and comparing the previously-stored excitation profile data with the excitation profile that has been obtained on the basis of the detection result.

A method of specifying the location and the concentration of the harmful substance is now described. FIG. 9 is a graph depicting a time-dependent waveform (LIDAR echo) of a resonance spectrum of a harmful substance. FIG. 9 represents a time-dependent waveform of a resonance Raman spectrum obtained when the harmful substance is excited by a single wavelength, and a time axis denotes an elapsed time from the moment of pulse oscillation in a laser source started. The distance to the harmful substance, i.e., the location of the harmful substance, can be determined by converting a time elapsed from the pulse oscillation to reception of the resonance Raman-scattered light into a distance by using the velocity of light. Furthermore, in the case of irradiating the same substance with the laser beam of the same wavelength, there is a relationship that the concentration of the irradiated substance increases as the intensity of the resonance Raman-scattered light increases. Accordingly, the concentration of the irradiated substance can be measured on the basis of the intensity of the resonance Raman-scattered light. When the location and the concentration of the irradiated substance are to be measured, it is not required to observe the time-dependent waveforms of all peaks of multiple resonance Raman shifts as illustrated in FIG. 9(A). For example, as illustrated in FIG. 9(B), the location and the concentration of the irradiated substance may be measured by determining the time-dependent waveform of a single peak that can be measured with maximum sensitivity.

Thus, the remote substance identification device 1 according to this embodiment includes the laser device 10 and the wavelength conversion device 20 that emit the laser beams of the wavelengths in the ultraviolet range to the irradiated object, the light collecting optical system 30, the spectrometric instrument 40, and the optical detector 50 that detect the resonance Raman-scattered light generated from the irradiated object due to the resonance Raman scattering, and the processor 60 that identifies the irradiated object on the basis of the detection result of the resonance Raman-scattered light. As described above, many harmful substances cause the electron energy level transitions in the ultraviolet range and exhibit the enhancement of the Raman-scattered light with the resonance of the Raman scattering. Therefore, the harmful substance (mixture) can be identified even from the remote location with high accuracy by, as in this embodiment, emitting the laser beams of the wavelengths in the ultraviolet range to the irradiated object and detecting the resonance Raman-scattered light generated from the irradiated object. For example, when the remote substance identification device 1 is used as illustrated in FIG. 6, a trace amount of the irradiated substance not more than several tens of ppm can be theoretically detected over a range of several tens to several hundreds of meters. Furthermore, because of using the laser beams of the wavelengths in the ultraviolet range in this embodiment, the measurement is performed in a solar blind area (i.e., a wavelength range not affected by the solar light that is background light), and the harmful substance can be detected with high accuracy even outdoors during the day.

Furthermore, the remote substance identification device 1 according to this embodiment includes the laser device 10 that oscillates the laser beam in the wavelength range higher than the ultraviolet range, and the wavelength conversion device 20 that converts the wavelength of the laser beam emitted from the laser device 10 into the wavelengths in the ultraviolet range. In this embodiment, therefore, the remote substance identification device 1 can emit the laser beams of various wavelengths and can identify the harmful substance with higher accuracy by detecting the resonance Raman-scattered light generated with the resonance Raman scattering for each wavelength.

Moreover, since the laser beam is emitted to the irradiated object after conversion into the different excitation wavelengths and the detection result of the resonance Raman-scattered light is obtained for each excitation wavelength, the three-dimensional resonance Raman spectrum (excitation profile) representing the excitation wavelength, the Raman shift, and the intensity of the resonance Raman-scattered light can be obtained as depicted in FIG. 7. As a result, the harmful substance can be identified with high accuracy even when it is a mixture.

In the remote substance identification device 1 according to this embodiment, the processor 60 previously stores plural types of the three-dimensional resonance Raman spectra (excitation profiles) in the storage device, and the spectrometric instrument 40 and the optical detector 50 identify the irradiated object by comparing the detected resonance Raman spectrum of the resonance Raman-scattered light generated from the irradiated object with the stored three-dimensional resonance Raman spectra (excitation profiles). Thus, by comparing with the stored three-dimensional resonance Raman spectra (excitation profiles) having features of the resonance Raman scattering of individual substances, the irradiated object can be identified with high accuracy even when substances having analogous chemical structures are present in the same space.

In addition, in the remote substance identification device 1 according to this embodiment, the concentration of the irradiated object is measured on the basis of the detected intensity of the resonance Raman-scattered light generated from the irradiated object. In the case of irradiating the same substance with the laser beam of the same wavelength, there is a relationship that the concentration of the irradiated substance increases as the intensity of the resonance Raman-scattered light increases. Accordingly, the concentration of the irradiated substance can be appropriately measured on the basis of the intensity of the resonance Raman-scattered light.

The remote substance identification device 1 according to this embodiment detects the resonance Raman-scattered lights that are generated upon the irradiation with the laser beams of the wavelengths in the ultraviolet range. As described above, various types of harmful substances cause the electron energy level transitions in the ultraviolet range and exhibit the enhancement of the Raman-scattered light with the resonance of the Raman scattering. Accordingly, the various types of harmful substance can be specified by detecting the resonance Raman-scattered lights generated upon the irradiation with the laser beams of the wavelengths in the ultraviolet range. Moreover, it is known that the Raman scattering spectroscopy can be applied to a wide variety of substances regardless of gases, liquids, and solids. In other words, the remote substance identification device 1 according to this embodiment can further identify liquid and solid harmful substances and harmful microorganisms in addition to gaseous harmful substance.

While the preferred embodiments of the present invention have been described above, the technical scope of the present invention is not limited to the matters described in the above embodiment. The above embodiment can be variously altered or improved, and modifications obtained by altering or improving the above embodiment also fall within the technical scope of the present invention.

For example, while the irradiated object is identified in the above embodiment by comparing the previously-stored resonance Raman spectra of the individual harmful substances and the detected resonance Raman spectrum of the irradiated object, the method of identifying the irradiated object is not limited to the above-described one. The irradiated object may be identified, by way of example, as follows. When the irradiated object has a relatively simple structure and there are a relatively small number of interference components in the environment, the resonance Raman spectrum exhibits only one peak. Accordingly, several to several tens of optical filters allowing respectively only the peak wavelengths of the resonance Raman-scattered lights generated from the individual harmful substances to pass therethrough may be prepared to detect the resonance Raman-scattered lights passing through the optical filters. When the resonance Raman-scattered light passing through any one of the optical filters has been detected, the irradiated object may be identified as the harmful substance corresponding to the relevant optical filter.

In the above embodiment, the mixture is identified by using data of the three-dimensional resonance Raman spectrum representing the excitation wavelength, the Raman shift, and the light intensity of the resonance Raman-scattered light as depicted in FIG. 7. However, the mixture may be identified by using data of two-dimensional resonance Raman spectrum representing the Raman shift and the light intensity at a predetermined excitation wavelength in the ultraviolet range. In such a case, identification accuracy of the mixture reduces in comparison with that in the case of using the data of the three-dimensional resonance Raman spectrum. However, a data processing speed can be increased with reduction in an amount of reference data to be stored in advance and an amount of data used in processing.

While the above embodiment has been described, by way of example, in connection with the case in which the laser beam having wavelength of 210 nm or longer is emitted, the present invention is not to such a case, and the remote substance identification device 1 may be constituted to emit the laser beam having wavelength shorter than 210 nm. In the latter case, a substance generating the resonance Raman-scattered light with the laser beam having wavelength shorter than 200 nm, such as hydrogen, can also be identified.

While, in the above embodiment, the LBO crystals 21 and 22 and the BBO crystals 235, 252 and 253 are used, by way of example, as nonlinear optical crystals for wavelength conversion, the present invention is not to such a case, and another type of nonlinear optical crystal may be used. Any suitable known method can also be used insofar as the method can sweep the wavelength of the laser beam over the ultraviolet wavelength range.

FIG. 10 is a block diagram of a laser device 110 and a wavelength conversion device 120 according to a first modification. The laser device 110 includes excitation light sources 111a and 111b, a laser medium 112, and a resonator (113 and 114). The wavelength conversion device 120 includes a second-harmonic generator 121, a third-harmonic generator 122, a fourth-harmonic generator 123, and a fifth-harmonic generator 124.

In the laser device 110 according to the first modification, flash lamps are used as the excitation light sources 111a and 111b. The laser medium 112 is a solid laser rod that emits a laser beam upon irradiation with excitation lights, and an Nd:YAG crystal is used as the laser medium 112 in the first modification. The resonator includes an output mirror 113 and a rear mirror 114, and the laser medium 112 is disposed between both the mirrors. Each excitation light source 111 is not limited to the above-mentioned example, and another type of energy source, such as a semiconductor laser, may be used instead.

A fundamental wave (1064 nm) directly output from the laser medium 112 is successively subjected to wavelength conversion in the second-through fifth-higher harmonic generators (121 to 124), and a laser beam having a desired wavelength after the conversion is output. The higher harmonic generators (121-124) are each a nonlinear optical crystal (e.g., an LBO crystal, a BBO crystal, or a KDP crystal) that converts an input wave under particular conditions regarding the direction of the plane of polarization and energy, for example, and generates a laser beam having wavelength different from that of the input wave. An optimum crystal in accordance with the laser medium and the application is used.

The second-higher harmonic generator 121 performs conversion into a second-higher harmonic (532 nm) by sum frequency generation using the fundamental wave (1064 nm) output from the laser medium 112, and then outputs the second-higher harmonic (532 nm).

The third-higher harmonic generator 122 outputs a third-higher harmonic (355 nm) by sum frequency generation using the fundamental wave (1064 nm) and the second-higher harmonic (532 nm) output from the second-higher harmonic generator 121.

The fourth-higher harmonic generator 123 performs conversion into a fourth-higher harmonic (266 nm) by sum frequency generation using the second-higher harmonic (532 nm) output from the second-higher harmonic generator 121, and then outputs the fourth-higher harmonic (266 nm).

The fifth-higher harmonic generator 124 outputs a fifth-higher harmonic (213 nm) by sum frequency generation using the fourth-higher harmonic (266 nm) output from the fourth-higher harmonic generator 123 and the fundamental wave (1064 nm) branched by a mirror optical system.

Laser crystals or optical fibers listed, by way of example, in Table 2 can be optionally used as the laser medium 112, and resonance excitation can be realized by selecting an optimum medium in accordance with a target substance to be identified. In Table 2, Nos. 1 to 8 represent materials each generating a fundamental wave of a single wavelength when excited under predetermined conditions, while Nos. 9 and 10 represent wavelength-variable laser crystals each capable of changing an oscillation wavelength. In the case of using the crystals of Nos. 9 and 10, unlike the wavelength variable type using an optical parametric oscillator in which an output wavelength is changed by driving a wavelength conversion crystal, the output wavelength can be varied by changing a laser wavelength of seed light.

TABLE 2

| Laser Crystal, No. etc. | Oscillation Wavelength [nm] | | | | |
|---|---|---|---|---|---|
| | 1ω | 2ω | 3ω | 4ω | 5ω |
| 1 Nd: YAG | 1064 | 532 | 355 | 266 | 213 |
| 2 Nd: YLF | 1047 | 524 | 349 | 262 | 209 |
| | 1053 | 527 | 351 | 263 | 211 |
| 3 Nd: glass | 1054 | 527 | 351 | 264 | 211 |
| | 1062 | 531 | 354 | 266 | 212 |
| 4 Nd: YVO$_4$ | 1065 | 533 | 355 | 266 | 213 |
| 5 Yb: YAG | 1030 | 515 | 343 | 258 | 206 |
| 6 Yb Doped Fiber | 1000 | 500 | 333 | 250 | 200 |
| 7 Er Doped Fiber | 1550 | 775 | 517 | 388 | 310 |
| 8 Er: YAG | 2940 | 1470 | 980 | 735 | 588 |
| 9 Alexandrite | 700-820 | 350-410 | 233-273 | 175-205 | 140-164 |
| 10 Ti: Sapphire | 650-1180 | 325-590 | 217-393 | 163-295 | 130-236 |

A remote substance identification device can be constituted by connecting the above-described laser device 110 and wavelength conversion device 120 according to the first modification to the above-described light collecting optical system 30, spectrometric instrument 40, optical detector 50, and processor 60. According to the first modification, three wavelengths (355 nm, 266 nm, and 213 nm) in the ultraviolet range can be output by one laser device.

Figure 11:
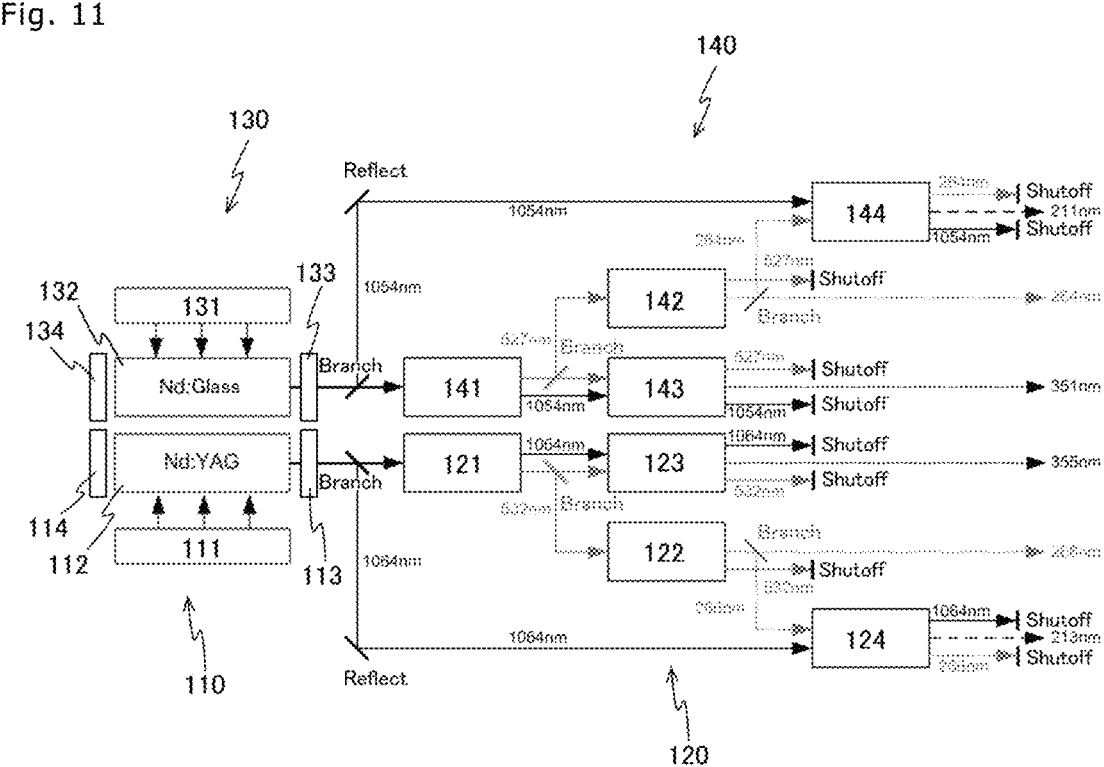
FIG. 11 is a block diagram of a laser device and a wavelength conversion device according to a second modification.

FIG. 11 is a block diagram of laser devices 110 and 130 and wavelength conversion devices 120 and 140 according to a second modification. The second modification can output laser beams of six wavelengths by installing two systems of laser devices and wavelength conversion devices.

The laser device 110 and the wavelength conversion device 120 have substantially the same configurations as those in the first modification.

The laser device 130 is different from the laser device 110 in using Nd:glass as a laser medium 132, but other points are the same as those in the laser device 110. Higher harmonic generators (141-144) are each a nonlinear optical crystal (e.g., an LBO crystal, a BBO crystal, or a KDP crystal) that generates a laser beam having wavelength different from that of an input wave.

The second-higher harmonic generator 141 performs conversion into a second-higher harmonic (527 nm) by sum frequency generation using a fundamental wave (1054 nm) output from the laser medium 132, and then outputs the second-higher harmonic (527 nm).

The third-higher harmonic generator 143 outputs a third-higher harmonic (351 nm) by sum frequency generation using the fundamental wave (1054 nm) and the second-higher harmonic (527 nm) output from the second-higher harmonic generator 141.

The fourth-harmonic generator 142 performs conversion into a fourth-higher harmonic (264 nm) by sum frequency generation using the second-higher harmonic (527 nm) output from the second-higher harmonic generator 141, and then outputs the fourth-higher harmonic (264 nm).

The fifth-harmonic generator 144 outputs a fifth-higher harmonic (211 nm) by sum frequency generation using the fourth-higher harmonic (264 nm) output from the fourth-higher harmonic generator 142 and the fundamental wave (1054 nm) branched by a mirror optical system.

A second irradiation system of the remote substance identification device can be constituted by connecting the above-described laser device 130 and wavelength conversion device 140 according to the second modification to the above-described light collecting optical system 30, spectrometric instrument 40, optical detector 50, and processor 60.

Here, a single set of the light collecting optical system 30, the spectrometric instrument 40, the optical detector 50, and the processor 60 can be shared by a plurality of irradiation systems. In addition to the three wavelengths that can be output in the first modification, other three different wavelengths (351 nm, 264 nm, and 211 nm) in the ultraviolet range can be output according to the second modification. By adding an irradiation system using suitable one or more of the laser crystals listed in Table 2, etc., it is also possible to further increase the number of oscillation wavelengths (namely, to install third and subsequent irradiation systems).

LIST OF REFERENCE SIGNS

1 . . . remote substance identification device
10 . . . laser device
20 . . . wavelength conversion device
21, 22 . . . LBO crystal
30 . . . light collecting optical system
40 . . . spectrometric instrument
50 . . . optical detector
60 . . . processor
70 . . . display device
110 . . . laser device (first modification)
120 . . . wavelength conversion device (first modification)
130 . . . laser device (second modification)
140 . . . wavelength conversion device (second modification)

The invention claimed is:
1. A remote substance identification device comprising:
a laser device including an oscillator that emits a laser beam of a particular wavelength;
a light collecting-detecting device that collects and detects resonance Raman-scattered light from an indoor or outdoor irradiated space; and
a processor configured to identify an irradiated object present in the irradiated space on the basis of a result detected by the light collecting-detecting device,
wherein the remote substance identification device further comprises a wavelength conversion device that converts a wavelength of the laser beam emitted from the laser device into a plurality of different wavelengths and that emits laser beams of the different wavelengths to the irradiated space,
the oscillator is an oscillator oscillating the laser beam in a wavelength range longer than an ultraviolet range,
the wavelength conversion device includes a first output system and a second output system,
the first output system converts the laser beam oscillated from the oscillator into a laser beam of shorter wavelength than a wavelength of the laser beam oscillated from the oscillator and outputs the converted laser beam either to the irradiated space or to the second output system in a switchable manner so that the laser beam from the first output system is output either to the irradiated space or to the second output system, and
the second output system converts the laser beam output from the first output system into a laser beam of shorter wavelength in the ultraviolet range than the wavelength of the laser beam output from the first output system and outputs the converted laser beam to the irradiated space, and
the processor is configured to identify the irradiated object on the basis of resonance Raman-scattered light attributable to the laser beam output from the second output system.

2. The remote substance identification device according to claim 1, wherein the second output system converts the laser beam output from the first output system into a laser beam having wavelength of 250 nm or shorter and outputs the converted laser beam.

3. The remote substance identification device according to claim 1, further comprising a scanning device that scans the irradiated space with the laser beams emitted from the wavelength conversion device, and
the processor further measures a location of the irradiated object on the basis of the result detected by the light collecting-detecting device.

4. The remote substance identification device according to claim 1, wherein the wavelength conversion device includes a wavelength converter to which the laser beam oscillated from the oscillator is input, and a rotating device that changes an inclination angle of the wavelength converter relative to an optical axis continuously or discontinuously in a stepwise manner.

5. The remote substance identification device according to claim 4, wherein the first output system is a first optical parametric oscillator that includes the rotating device and that converts the laser beam oscillated from the oscillator into the laser beam of shorter wavelength and outputs the converted laser beam,
the second output system is a second optical parametric oscillator that converts the laser beam output from the first optical parametric oscillator into a laser beam of double frequency and outputs the converted laser beam, and
the remote substance identification device further includes a mirror that passes the laser beam output from the first optical parametric oscillator therethrough when wavelength of the output laser beam is 420 nm or longer, and reflects the laser beam output from the first optical parametric oscillator to enter the second optical parametric oscillator when the wavelength of the output laser beam is shorter than 420 nm.

6. The remote substance identification device according to claim 1, wherein the wavelength conversion device includes a second-higher harmonic generator that converts the laser beam oscillated from the oscillator into a second-higher harmonic laser beam and outputs the converted second-higher harmonic laser beam, a third-higher harmonic generator that converts the laser beam output from the second-higher harmonic generator into a third-higher harmonic laser beam and outputs the converted third-higher harmonic laser beam, and a fourth-higher harmonic generator that converts the laser beam output from the third-harmonic generator into a fourth-higher harmonic laser beam and outputs the converted fourth-harmonic laser beam, and
the third-higher harmonic generator constitutes the first output system, and the fourth-higher harmonic generator constitutes the second output system.

7. The remote substance identification device according to claim 6, wherein the wavelength conversion device further includes a fifth-harmonic generator that converts the laser beam output from the fourth-higher harmonic generator into a fifth-higher harmonic laser beam and outputs the converted fifth-higher harmonic laser beam, and
the fifth-higher harmonic generator constitutes the third output system, and the processor identifies the irradiated objects on the basis of resonance Raman-scattered lights attributable to the laser beams output from the first through third output systems.

8. The remote substance identification device according to claim 1, comprising a plurality of irradiation systems each including the laser device and the wavelength conversion device, the irradiation systems emitting laser beams of which wavelengths do not overlap with each other, wherein the processor identifies the irradiated objects on the basis of resonance Raman-scattered lights attributable to the laser beams output from the plurality of irradiation systems.

9. The remote substance identification device according to claim 1, wherein the processor includes a storage device that previously stores an excitation profile representing a feature pattern of the resonance Raman-scattered light at an excitation wavelength for each substance, and
the processor classifies and identifies individual substances in the irradiated object in form of a mixture by comparing the result detected by the light collecting-detecting device and the excitation profile.

10. The remote substance identification device according to claim 1, wherein the light collecting-detecting device includes a first optical filter allowing only a first wavelength range to pass therethrough and a second optical filter allowing only a second wavelength range to pass therethrough, the second wavelength range having a center wavelength different from that of the first wavelength range, and
the processor identifies the irradiated object on the basis of a correspondence relationship between the wavelength range passing through each of the optical filters and a wavelength of the resonance Raman-scattered light generated from each irradiated object.

11. The remote substance identification device according to claim 1, wherein the processor measures a concentration of the irradiated object on the basis of the intensity of the detected Raman-scattered light from the irradiated object.

12. The remote substance identification device according to claim 1, wherein the irradiated object is a gaseous harmful substance, a liquid harmful substance, a solid harmful substance, or a harmful microorganism.

13. The remote substance identification device according to claim 12, wherein the irradiated object is $H_2S$, $SO_2$, COS, HCL, $NH_3$, $CL_2$, tabun, sarin, soman, cyclosarin, or a mimic in air.

14. A remote substance identification method of emitting a laser beam to an indoor or outdoor irradiated space, collecting and detecting resonance Raman-scattered light from an irradiated object present in the irradiated space, and determining a location of the irradiated object on the basis of the resonance Raman-scattered light, the remote substance identification method comprising steps of:
emitting laser beams of different wavelengths by using the remote substance identification device of claim 1, and classifying and identifying, by using the remote substance identification device of claim 1, individual substances in the irradiated object in form of a mixture on the basis of detected results of the resonance Raman-scattered lights generated upon irradiation with the laser beams of the different wavelengths.

15. The remote substance identification method according to claim 14, wherein the irradiated space is an outdoor space, and
the location and a concentration of the irradiated object present in the irradiated space are detected by scanning the irradiated space with the laser beams.

* * * * *